(12) United States Patent
Lynott

(10) Patent No.: US 6,428,495 B1
(45) Date of Patent: Aug. 6, 2002

(54) HAMSTRING BRACE

(76) Inventor: John P. Lynott, 25417 K-22 Box 2, Merrill, IA (US) 51038

( * ) Notice: Subject to any disclaimer, the term of this patent is extended or adjusted under 35 U.S.C. 154(b) by 0 days.

(21) Appl. No.: 09/426,159

(22) Filed: Oct. 22, 1999

(51) Int. Cl.[7] .............................. A61F 5/00; A61F 5/37; A63B 21/02
(52) U.S. Cl. .............................. 602/23; 602/4; 128/875; 482/124
(58) Field of Search .............................. 602/5, 4, 23–25, 602/19, 60–62; 482/124, 105; 128/845, 846, 869, 875, 882, 876; 2/303, 309, 311, 313, 117, 240, 306, 329, 335, 340

(56) References Cited

U.S. PATENT DOCUMENTS

| | | | | |
|---|---|---|---|---|
| 807,908 A | * | 12/1905 | Bradstreet | 482/51 |
| 1,015,054 A | * | 1/1912 | McBride | |
| 1,377,031 A | * | 5/1921 | Silva | |
| 1,618,273 A | * | 2/1927 | Davidson | 482/124 |
| 5,186,701 A | * | 2/1993 | Wilkinson | 482/125 |
| 5,362,295 A | * | 11/1994 | Nurge | 482/124 |
| 5,647,827 A | * | 7/1997 | Gutkowski | 482/124 |
| 5,716,307 A | * | 2/1998 | Vadher | 482/125 |
| 5,745,917 A | * | 5/1998 | Dicker et al. | 482/105 X |
| 5,882,321 A | * | 3/1999 | Fisk | 602/4 |
| 5,993,362 A | * | 11/1999 | Ghobadi | 482/124 |
| 6,213,922 B1 | * | 4/2001 | Afanasenko et al. | 482/124 |

* cited by examiner

Primary Examiner—Denise M. Pothier

(57) ABSTRACT

A hamstring brace for supporting the hamstring muscle either during recovery from an injury or during strenuous activity to prevent an injury includes a waistband, adjustable elastic bands, an adjustable lateral support band, and optionally an adjustable stirrup assembly. Multiple ring pairs are provided on the waistband to permit lateral adjustment of the elastic bands along the waistband. The leg strap assembly also includes a spacer strap and lateral patellar support straps that work in combination with the lateral support band to attach the hamstring brace below the knee without putting direct pressure on the patella. Multiple straps and clips provide maximum adjustability.

17 Claims, 3 Drawing Sheets

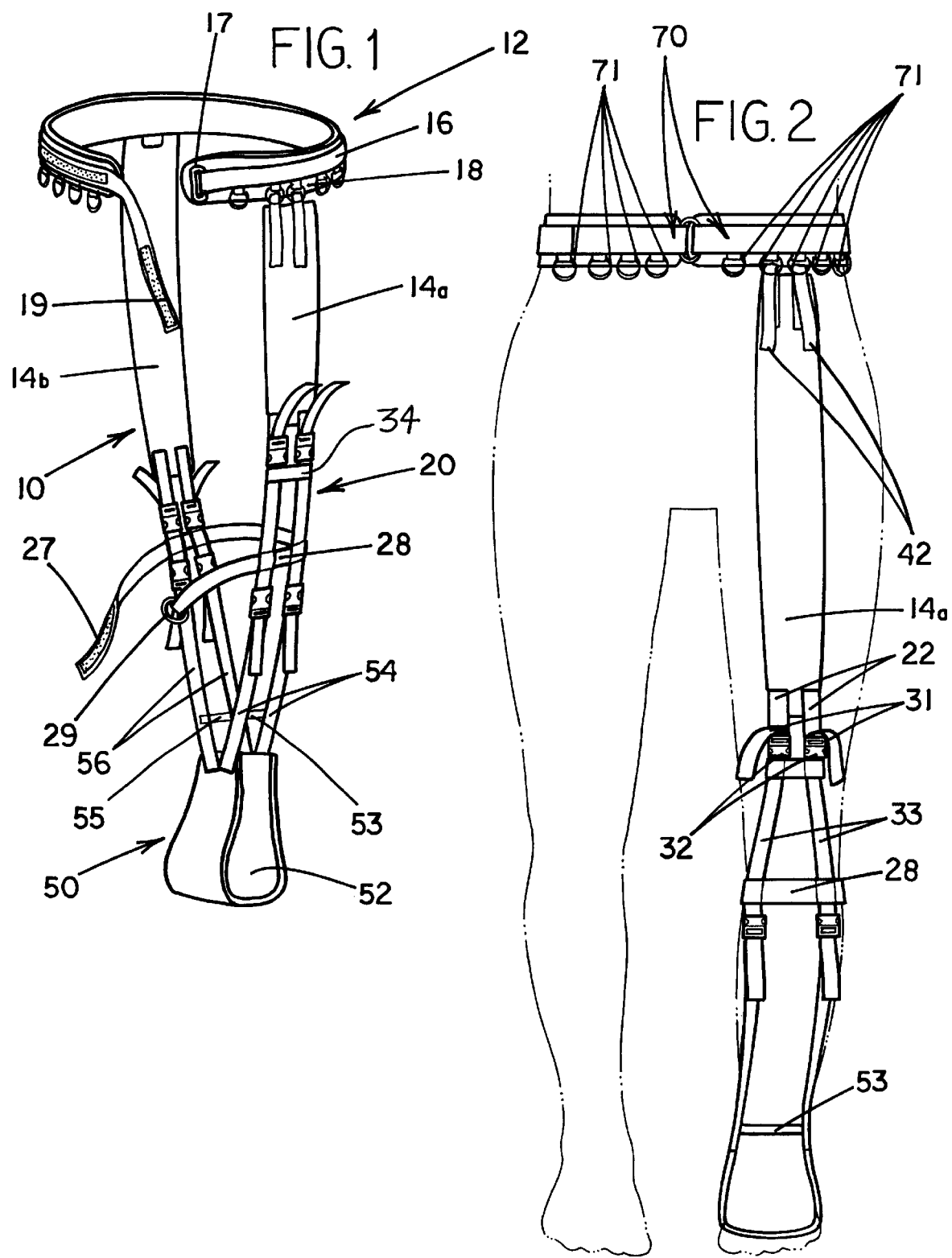

HAMSTRING BRACE

BACKGROUND OF THE INVENTION

1. Field of the Invention

The present invention relates to braces and more particularly pertains to a new hamstring brace for supporting the hamstring muscle either during recovery from an injury or during strenuous activity to prevent an injury.

2. Description of the Prior Art

The use of braces is known in the prior art. More specifically, braces heretofore devised and utilized are known to consist basically of familiar, expected and obvious structural configurations, not withstanding the myriad of designs encompassed by the crowded prior art which have been developed for the fulfillment of countless objectives and requirements.

Known prior art includes U.S. Pats. No. 1,269,829; 4,180,261; 2,166,809; 4,252,112; 5,145,027; 2,740,969; 1,548,711; 5,445,114; 2,433,262; 5,256,119; 5,615,750; 1,262,804; 4,709,692; 2,344,031; and U.S. Pat. No. Des. 166,758.

While these devices fulfill their respective, particular objectives and requirements, the aforementioned patents do not disclose a new hamstring brace. The inventive device includes a waistband, adjustable elastic bands, an adjustable lateral support band, and an adjustable stirrup assembly.

In these respects, the hamstring brace according to the present invention substantially departs from the conventional concepts and designs of the prior art, and in so doing provides an apparatus primarily developed for the purpose of supporting the hamstring muscle either during recovery from an injury or during strenuous activity to prevent an injury.

SUMMARY OF THE INVENTION

In view of the foregoing disadvantages inherent in the known types of braces now present in the prior art, the present invention provides a new hamstring brace construction wherein the same can be utilized for supporting the hamstring muscle either during recovery from an injury or during strenuous activity to prevent an injury.

The general purpose of the present invention, which will be described subsequently in greater detail, is to provide a new hamstring brace apparatus and method which has many of the advantages of the braces mentioned heretofore and many novel features that result in a new hamstring brace which is not anticipated, rendered obvious, suggested, or even implied by any of the prior art braces, either alone or in any combination thereof.

To attain this, the present invention generally comprises a waistband, adjustable elastic bands, an adjustable lateral support band, and an adjustable stirrup assembly.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new hamstring brace apparatus and method which has many of the advantages of the braces mentioned heretofore and many novel features that result in a new hamstring brace which is not anticipated, rendered obvious, suggested, or even implied by any of the prior art braces, either alone or in any combination thereof.

It is another object of the present invention to provide a new hamstring brace that may be easily and efficiently manufactured and marketed.

It is a further object of the present invention to provide a new hamstring brace that is of a durable and reliable construction.

An even further object of the present invention is to provide a new hamstring brace which is susceptible of a low cost of manufacture with regard to both materials and labor, and which accordingly is then susceptible of low prices of sale to the consuming public, thereby making such hamstring brace economically available to the buying public.

Still yet another object of the present invention is to provide a new hamstring brace which provides in the apparatuses and methods of the prior art some of the advantages thereof, while simultaneously overcoming some of the disadvantages normally associated therewith.

Still another object of the present invention is to provide a new hamstring brace for supporting the hamstring muscle either during recovery from an injury or during strenuous activity to prevent an injury.

Yet another object of the present invention is to provide a new hamstring brace which includes a waistband, adjustable elastic bands, an adjustable lateral support band, and an adjustable stirrup assembly.

Still yet another object of the present invention is to provide a new hamstring brace that supports the knee joint while diminishing stress on the hamstring muscle.

Even still another object of the present invention is to provide a new hamstring brace that provides elastic support to the hamstring muscle to facilitate increased motor function of the leg after an injury.

Yet still another object of the present invention is to provide a hamstring brace that facilitates recovery from a hamstring injury.

Still even another object of the present invention is to provide a hamstring brace that enhances the mobility of a person with a hamstring injury.

Even yet another object of the present invention is to provide a hamstring brace that provides support of the hamstring muscle and reduces stress on the hamstring muscle to decrease the chance of injury to the hamstring muscle during strenuous activity.

Yet still another object of the invention is to provide a hamstring brace for facilitating freedom of movement and recovery for health related problems normally restricting movement of the legs, particularly but not limited to stroke victims suffering partial paralysis.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new hamstring brace according to the present invention.

FIG. 2 is a front view of the present invention.

DESCRIPTION OF THE PREFERRED EMBODIMENT

Figure 3:
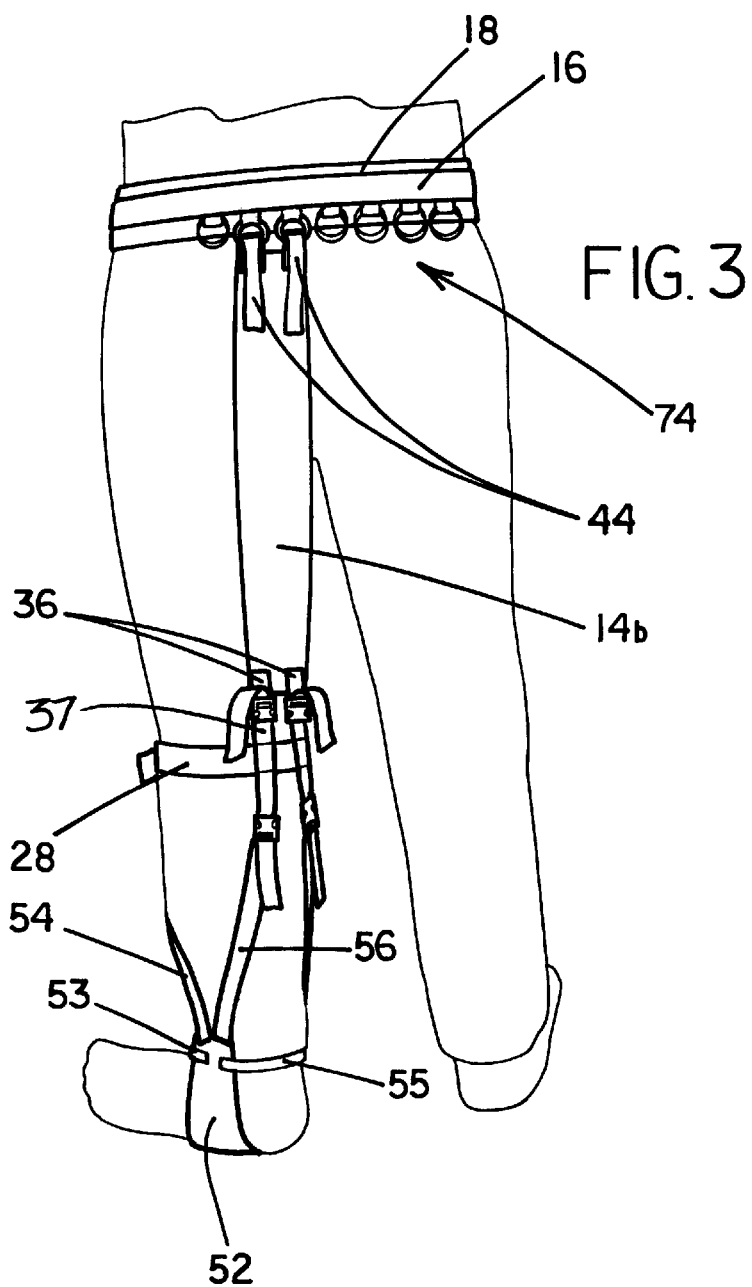
FIG. 3 is a rear view of the present invention.
Figure 4:
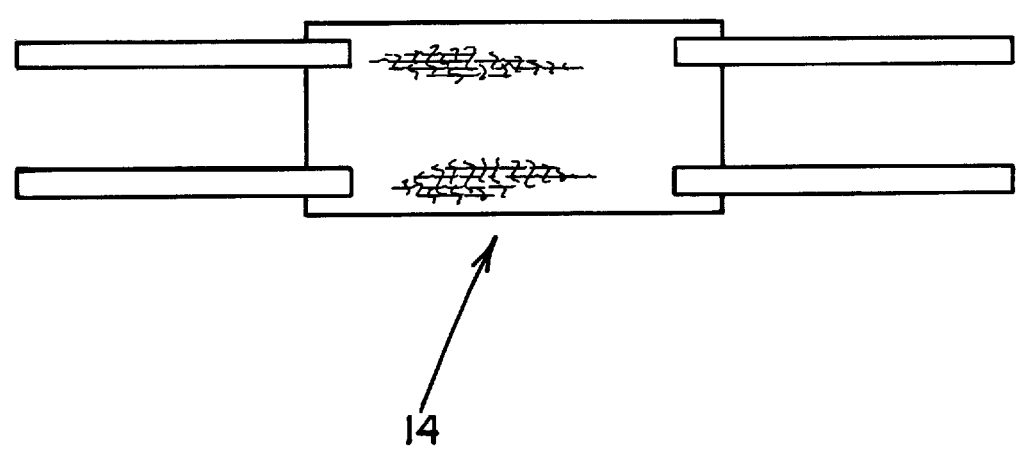
FIG. 4 is a front view of the interchangeable elastic bands present invention.
Figure 5:
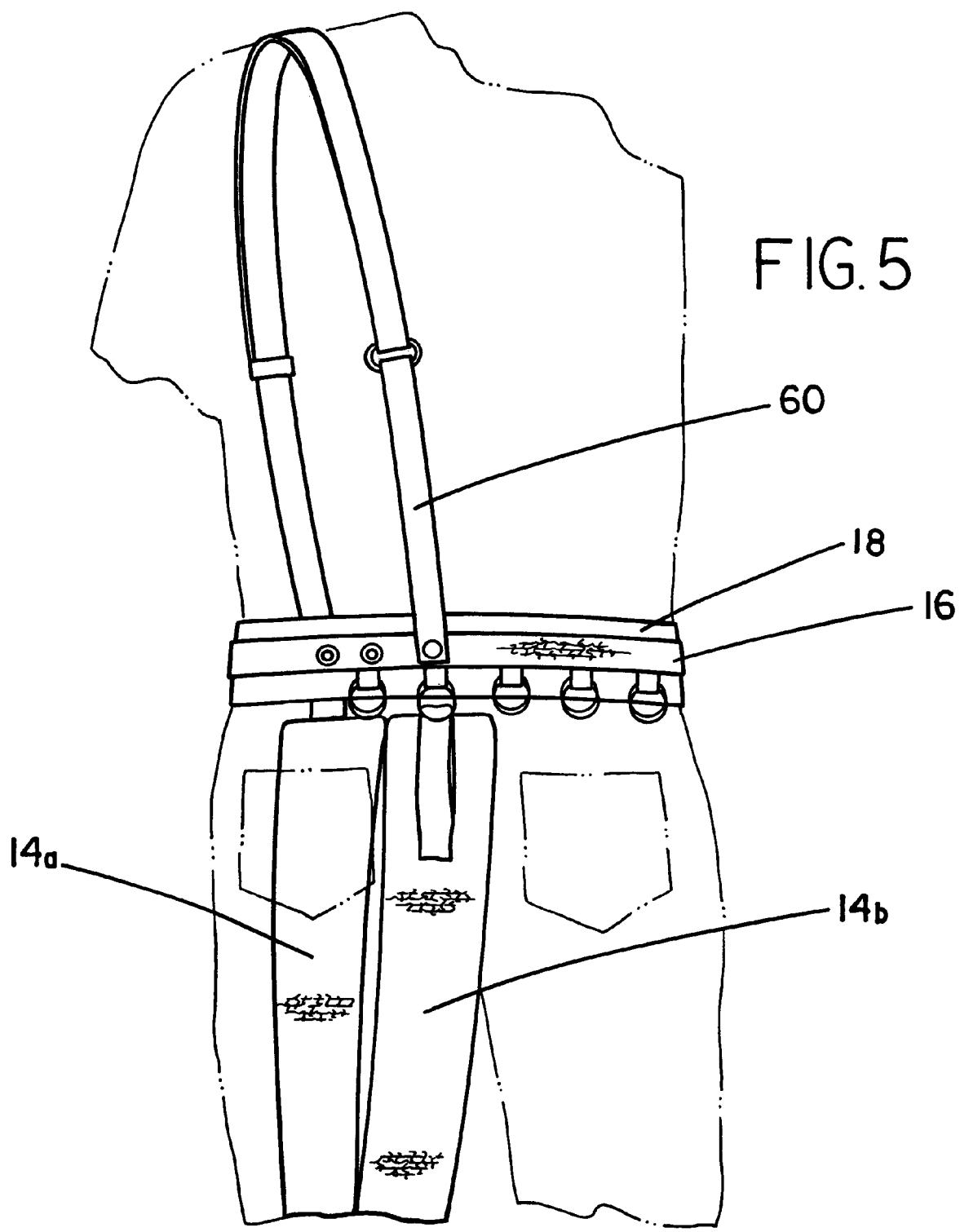
FIG. 5 is a rear view of the present invention.

With reference now to the drawings, and in particular to FIGS. 1 through 5 thereof, a new hamstring brace embodying the principles and concepts of the present invention and generally designated by the reference numeral 10 will be described.

As best illustrated in FIGS. 1 through 5, the hamstring brace 10 generally comprises a waistband 12, a plurality of elastic bands 14 coupled to the waistband 12, a leg strap assembly 20 coupled to the elastic bands 14 including a lateral support band 28. In various embodiments of the invention, the elastic bands may comprise a combination of the following types of materials as desired: elastic cloth, bungee cord, and isometric tubing or bands.

The leg strap assembly 20 is designed for attachment to the leg of the user such that the lateral support band 28 is positioned below a knee of the user. Thus tension in the elastic bands 14 provides an upward force on the lateral support strap 28 such that the waistband 12 partially supports the weight of the user's leg during movement whereby stress on the hamstring muscle is reduced.

The waistband 20 preferably includes an inelastic strap 16 coupled to a padding member 18 designed for positioning between the user and the inelastic strap 16 when the waistband is worn.

For adjustable attachment to the waist of the wearer the inelastic strap has a loop 17 at a first end and hook and loop fasteners 19 positioned at a second end. The waistband is securable by inserting the second end through the loop 17 and folding the second end over on itself to engage the hook and loop fasteners 19 to each other.

The elastic bands 14 generally include a frontal elastic band 14A and a posterior elastic band 14B. It is most preferable for the posterior elastic band 14B to have a greater length than the frontal elastic band 14A to permit room for the leg strap assembly 20 to encircle the patella as described below without putting direct pressure on the patella. Accordingly, the posterior elastic band 14B preferably has greater elasticity relative to the frontal elastic band 14A to compensate for the difference in length of the elastic bands 14A and 14B. Additionally, the elastic bands 14 are selectable from bands 14 having various lengths and elasticity to adjust the relative tension between the frontal elastic band 14A and the posterior elastic band 14B to accommodate the preferences of the user. The bands 14 may also be interchanged to reduce the elasticity of both bands as an injury to the hamstring heals and less support is needed.

The leg strap assembly 20 includes at least one frontal leg strap 22 but most preferably includes a pair of frontal leg straps 22 coupled to the frontal elastic band 14A. The knee accommodating assembly 30 is coupled to the frontal leg straps 22 by a first clip member 31 adjustably coupled to the each frontal leg strap 22 and a second clip member 32 for engaging the first clip member 31. A pair of lateral patellar support straps 33 are coupled to the second clip members 32, and a spacer strap 34 extends between the lateral patellar support straps 33. The spacer strap 34 is adapted for positioning above the patella of the user. The lateral patellar support straps 33 are adapted for positioning on opposing sides of the patella of the user. The lateral support band 28 is coupled to the lateral patellar support straps 33 such that the lateral support band 28, the lateral patellar support straps 33 and the spacer strap 34 generally surround the patella.

Similarly, at least one posterior leg strap 36 is coupled to the posterior elastic band 14B, but preferably a pair of posterior leg straps 36 are used. First clips 31 and second clips 32 are similarly used to couple the posterior leg straps 36 to respective posterior support straps 37. The lateral support band 28 is coupled to the posterior support straps 37 and includes hook and loop fasteners 27 and a lateral support band ring 29 for adjustably securing the lateral support band 28 around the leg of the wearer below the knee.

Optionally, a stirrup assembly 50 is attachable to the leg strap assembly 20. The stirrup assembly 50 is designed for receiving a foot of the user to provide additional support to the lower leg. The stirrup assembly 50 includes a stirrup member 52, a pair of frontal stirrup straps 54, a frontal stirrup strap stabilizing strap 53 extending between the frontal stirrup straps 54, a pair of posterior stirrup straps 56, and a posterior stirrup strap stabilizing strap 55 extending between the posterior stirrup straps. Alternately, the stirrup stabilizing straps 53 and 55 can be positioned to extend between upper portions of the stirrup member 52 as shown in FIG. 3.

A further option is to include an adjustable shoulder strap 60 that is coupled to the waistband 12. The shoulder strap 60 is designed for distributing a portion of the tension on the waistband 12 to a shoulder of the user to reduce hip strain.

To provide lateral adjustment of the elastic bands 14A and 14B, the method for coupling the bands 14A and 14B to the waistband 12 includes a first plurality of ring pairs 70 generally horizontally aligned on the waistband 12. The frontal elastic band 14A is then couplable to the waistband 12 by inserting each frontal connecting strap 42 through one selectable pair of rings 71 whereby the position of the frontal elastic band 14A is laterally adjustable by coupling the frontal connecting straps 42 to a selected pair of the first plurality of ring pairs 70.

Similarly, the posterior elastic band 14B is adjustable using a second plurality of ring pairs 74 horizontally aligned on the waistband 12 and a pair of posterior connecting straps 44 coupled to the posterior elastic band 14B.

It has also been found that the preferred width of elastic band is between 3 and 5 inches and the clips are preferably between 1 to 3 inches in width. Further, although pairs of clips are preferred proximate the base of the elastic bands 14A and 14B, a single frontal leg strap and single posterior leg strap may be used with some reduction in adjustability but enhanced simplicity of fitting the brace to the user.

The pair of connecting straps 42 has been employed to facilitate smaller lateral adjustments between ring pairs 71 along the waistband. Alternatively, a single broad connecting strap may be used. It remains preferable to use rings along the waistband because they are less susceptible to breakage than the clips when they are accidentally struck and the rings are less likely to injure an arm or hand of the wearer if the arm or hand comes into accidental contact with the unused rings.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A hamstring brace for attaching to a leg of a user to alleviate pressure on a hamstring of a wearer, the hamstring brace comprising:

a waistband;

a plurality of elastic bands, each elastic band being coupled to the waistband;

a leg strap assembly adapted for attachment to the leg of the user, the leg strap assembly being coupled to the elastic bands;

said leg strap assembly including a lateral support band, said lateral support band being adapted for attachment to the leg of the user such that the lateral support band is positioned immediately below a knee of the user whereby a tensile force is provided between said waistband and said lateral support band for alleviating pressure on the hamstring;

a first one of said elastic bands being coupled between a front portion of said waistband and a front portion of said lateral support band such that said first one of said elastic bands is adapted for positioning to extend along a front of a thigh of the user;

a second one of said elastic bands being coupled between a rear portion of said waistband and a rear portion of said lateral support band such that said second one of said elastic bands is adapted for positioning to extend along a rear of the thigh of the user; and wherein said first one of said elastic bands includes a frontal elastic band and said second one of said elastic bands includes a posterior elastic band, the posterior elastic band having a greater length and elasticity than the frontal elastic band whereby the frontal elastic band permits room for said leg strap assembly to encircle the patella without putting direct pressure on the patella during use;

wherein said leg strap assembly further comprises:

at least one frontal leg strap coupled to said first one of said plurality of elastic bands;

a knee accommodating assembly coupled to said frontal leg strap, said knee accommodating assembly including a spacer strap and a pair of lateral patellar support straps, said spacer strap being adapted for positioning above the patella of the user, said lateral patellar support straps being adapted for positioning on opposing sides of the patella of the user such that said lateral patellar support straps prevent lateral movement of said knee accommodating assembly relative to the patella of the user, wherein said spacer strap extends between said lateral patellar support straps for facilitating maintenance of the lateral patellar support straps on opposing sides of the patella of the user; and said lateral patellar support straps being coupled to said lateral support band.

2. The hamstring brace of claim 1, further comprising:

said waistband including an inelastic strap coupled to a padding member, said padding member being for positioning between the user and said inelastic strap when said waistband is being worn;

said inelastic strap having a loop at a first end;

said inelastic strap further having hook and loop fasteners positioned at a second end such that said second end is engageable around said loop such that said waistband forms a ring whereby said waistband is engageable around a waist of the user.

3. The hamstring brace of claim 1, further comprising:

a first pair of rings coupled to said waistband, said first pair of rings engaging a first connecting strap, said first connecting strap being coupled to said first one of said elastic bands, said first pair of rings being positioned on said waistband such that said first one of said elastic bands is adapted to extend downwardly from said waistband along the front of the thigh of the user when worn by the user; and a second pair of rings coupled to said waistband, said second pair of rings engaging a second connecting strap, said second connecting strap being coupled to said second one of said elastic bands, said second pair of rings being positioned on said waistband such that said second one of said elastic bands is adapted to extend downwardly from said waistband along the rear of the thigh of the user when worn by the user.

4. The hamstring brace of claim 1, wherein said leg strap assembly further comprises:

at least one posterior leg strap coupled to said second one of said elastic bands;

a posterior support strap coupled to said posterior leg strap; and said lateral support band being coupled to said posterior support strap.

5. The hamstring brace of claim 4, further comprising:
each said posterior leg strap including a first clip member;
an associated second clip member for each first clip member being adjustably coupled to said second elastic band, each first clip member being lockingly engageable to said associated second clip member whereby said second elastic band is coupled to said leg strap assembly.

6. The hamstring brace of claim 1 further comprising:
a stirrup assembly adapted for receiving a foot of the user therein, the stirrup assembly being coupled to said leg strap assembly, said stirrup assembly being for distributing a portion of tension on said lateral support strap to the foot of the user.

7. The hamstring brace of claim 6 further comprising:
said stirrup assembly including a stirrup member, a pair of frontal stirrup straps, a frontal stirrup strap stabilizing strap extending between said frontal stirrup straps, a pair of posterior stirrup straps, and a posterior stirrup strap stabilizing strap extending between said posterior stirrup straps.

8. The hamstring brace of claim 1, further comprising:
an adjustable shoulder strap coupled to said waistband, said shoulder strap being for distributing a portion of the tension on said waistband to a shoulder of the user.

9. The hamstring brace of claim 1, further comprising:
a first plurality of ring pairs coupled to said waistband, said first plurality of ring pairs being generally horizontally aligned on said waistband;
wherein said first one of said elastic bands is couplable to said waistband by a pair of frontal connecting straps coupled to said first elastic band, said first elastic band being laterally adjustable by coupling said frontal connecting straps to a selected pair of said first plurality of ring pairs;
a second plurality of ring pairs coupled to said waistband, said second plurality of ring pairs being generally horizontally aligned on said waistband; and
wherein said second one of said elastic bands is couplable to said waistband by a pair of posterior connecting straps coupled to said second elastic band, said second elastic band being laterally adjustable by coupling said posterior connecting straps to a selected pair of said second plurality of ring pairs.

10. The hamstring brace of claim 1, further comprising:
each said frontal leg strap including a first clip member;
an associated second clip member for each first clip member being adjustably coupled to said first elastic band, each first clip member being lockingly engageable to said associated second clip member whereby said first elastic band is couplable to said leg strap assembly.

11. The hamstring brace of claim 1, further comprising:
said plurality of elastic bands coupled to said waistband being selectable from a set of interchangeable elastic bands including elastic bands of various lengths and elasticity such that the support provided by the hamstring brace is adjustable depending on the elasticity and length of the plurality of elastic bands selected.

12. A hamstring brace for attaching to a leg of a user, the hamstring brace comprising:
a waistband;
a plurality of elastic bands, each elastic band being coupled to the waistband;
a leg strap assembly adapted for attachment to the leg of the user, the leg strap assembly being coupled to the elastic bands; and
said leg strap assembly including a lateral support band, said lateral support band being adapted for attachment to the leg of the user such that the lateral support band is positioned below a knee of the user;
said waistband including an inelastic strap coupled to a padding member, said padding member being for positioning between the user and said inelastic strap when said waistband is being worn;
said inelastic strap having a loop at a first end;
said inelastic strap further having hook and loop fasteners positioned at a second end such that said second end is engageable around said loop such that said waistband forms a ring whereby said waistband is engageable around a waist of the user;
wherein said leg strap assembly further includes
a frontal leg strap coupled to a first one of said plurality of elastic bands,
a knee accommodating assembly coupled to said frontal leg strap, said knee accommodating assembly including a spacer strap and a pair of lateral patellar support straps, said spacer strap being adapted for positioning above the patella of the user, said lateral patellar support straps being adapted for positioning on opposing sides of the patella of the user, wherein said spacer strap extends between said lateral patellar support straps for facilitating maintenance of the lateral patellar support straps on opposing sides of the patella of the user,
said lateral patellar support straps being coupled to said lateral support band,
a posterior leg strap coupled to a second one of said plurality of elastic bands,
a posterior support strap coupled to said posterior leg strap, and
said lateral support band being coupled to said posterior support strap;
a stirrup assembly adapted for receiving a foot of the user therein, the stirrup assembly being coupled to said leg strap assembly;
said stirrup assembly including a stirrup member, a pair of frontal stirrup straps, a frontal stirrup strap stabilizing strap extending between said frontal stirrup straps, a pair of posterior stirrup straps, and a posterior stirrup strap stabilizing strap extending between said posterior stirrup straps;
an adjustable shoulder strap coupled to said waistband, said shoulder strap being for distributing a portion of the tension on said waistband to a shoulder of the user;
a first plurality of ring pairs coupled to said waistband, said first plurality of ring pairs being generally horizontally aligned on said waistband;
wherein said first one of said elastic bands is couplable to said waistband by a pair of frontal connecting straps coupled to said first elastic band, said first elastic band being laterally adjustable by coupling said frontal connecting straps to a selected pair of said first plurality of ring pairs;
a second plurality of ring pairs coupled to said waistband, said second plurality of ring pairs being generally horizontally aligned on said waistband;
wherein said second one of said elastic bands is couplable to said waistband by a pair of posterior connecting straps coupled to said second elastic band, said second elastic band being laterally adjustable by coupling said posterior connecting straps to a selected pair of said second plurality of ring pairs;

each said frontal leg strap including a first frontal clip member;

an associated second frontal clip member for each first frontal clip member being adjustably coupled to said first elastic band, each first frontal clip member being lockingly engageable to said associated second frontal clip member whereby said first elastic band is couplable to said leg strap assembly;

each said posterior leg strap including a first posterior clip member;

an associated second posterior clip member for each first posterior clip member being adjustably coupled to said second elastic band, each first posterior clip member being lockingly engageable to said associated second posterior clip member whereby said second elastic band is couplable to said leg strap assembly; and said plurality of elastic bands coupled to said waistband being selectable from a set of interchangeable elastic bands including elastic bands of various lengths and elasticity such that the support provided by the hamstring brace is adjustable depending on the elasticity and length of the plurality of elastic bands selected.

13. A hamstring brace for attaching to a leg of a user to alleviate pressure on a hamstring of a wearer, the hamstring brace comprising:

a waistband;

a plurality of elastic bands, each elastic band being coupled to the waistband;

a leg strap assembly adapted for attachment to the leg of the user, the leg strap assembly being coupled to the elastic bands;

said leg strap assembly including a lateral support band, said lateral support band being adapted for attachment to the leg of the user such that the lateral support band is positioned immediately below a knee of the user whereby a tensile force is provided between said waistband and said lateral support band for alleviating pressure on the hamstring;

a first one of said elastic bands being coupled between a front portion of said waistband and a front portion of said lateral support band such that said first one of said elastic bands is adapted for positioning to extend along a front of a thigh of the user;

a second one of said elastic bands being coupled between a rear portion of said waistband and a rear portion of said lateral support band such that said second one of said elastic bands is adapted for positioning to extend along a rear of the thigh of the user; and wherein said first one of said elastic bands includes a frontal elastic band and said second one of said elastic bands includes a posterior elastic band, the posterior elastic band having a greater length and elasticity than the frontal elastic band whereby the frontal elastic band permits room for said leg strap assembly to encircle the patella without putting direct pressure on the patella during use;

a stirrup assembly adapted for receiving a foot of the user therein, the stirrup assembly being coupled to said leg strap assembly, said stirrup assembly being for distributing a portion of tension on said lateral support strap to the foot of the user; and said stirrup assembly including a stirrup member, a pair of frontal stirrup straps, a frontal stirrup strap stabilizing strap extending between said frontal stirrup straps, a pair of posterior stirrup straps, and a posterior stirrup strap stabilizing strap extending between said posterior stirrup straps.

14. The hamstring brace of claim 13, further comprising:

said waistband including an inelastic strap coupled to a padding member, said padding member being for positioning between the user and said inelastic strap when said waistband is being worn;

said inelastic strap having a loop at a first end;

said inelastic strap further having hook and loop fasteners positioned at a second end such that said second end is engageable around said loop such that said waistband forms a ring whereby said waistband is engageable around a waist of the user.

15. The hamstring brace of claim 13, further comprising:

an adjustable shoulder strap coupled to said waistband, said shoulder strap being for distributing a portion of the tension on said waistband to a shoulder of the user.

16. The hamstring brace of claim 13, further comprising:

a first plurality of ring pairs coupled to said waistband, said first plurality of ring pairs being generally horizontally aligned on said waistband;

wherein said first one of said elastic bands is couplable to said waistband by a pair of frontal connecting straps coupled to said first elastic band, said first elastic band being laterally adjustable by coupling said frontal connecting straps to a selected pair of said first plurality of ring pairs;

a second plurality of ring pairs coupled to said waistband, said second plurality of ring pairs being generally horizontally aligned on said waistband; and wherein said second one of said elastic bands is couplable to said waistband by a pair of posterior connecting straps coupled to said second elastic band, said second elastic band being laterally adjustable by coupling said posterior connecting straps to a selected pair of said second plurality of ring pairs.

17. The hamstring brace of claim 13, further comprising:

said plurality of elastic bands coupled to said waistband being selectable from a set of interchangeable elastic bands including elastic bands of various lengths and elasticity such that the support provided by the hamstring brace is adjustable depending on the elasticity and length of the plurality of elastic bands selected.

* * * * *